United States Patent [19]

Felix

[11] 4,265,658

[45] May 5, 1981

[54] NOVEL CYCLOHEXENONE AMINO PHENYL AMIDES AND THEIR USE AS HERBICIDES

[75] Inventor: Raymond A. Felix, Richmond, Calif.

[73] Assignee: Stauffer Chemical Company, Richmond, Calif.

[21] Appl. No.: 944,047

[22] Filed: Sep. 20, 1978

[51] Int. Cl.³ .............. A01N 37/18; A01N 47/30; C07C 127/15; C07C 103/27

[52] U.S. Cl. ..................... 71/118; 71/120; 564/50; 564/152; 564/157; 564/190; 564/221

[58] Field of Search .......... 71/118, 121, 120, 123; 260/562 R, 553 A, 562 K

[56] References Cited

U.S. PATENT DOCUMENTS

| | | | |
|---|---|---|---|
| 3,281,467 | 10/1966 | Wilson et al. | 260/562 R |
| 3,360,359 | 12/1967 | Gilbert et al. | 71/123 |
| 3,396,005 | 8/1968 | Popoff | 71/120 |
| 3,407,056 | 10/1968 | Schwartz | 71/118 |
| 3,484,484 | 12/1969 | Schwartz et al. | 71/120 |
| 3,484,485 | 12/1969 | Schwartz | 71/118 |
| 3,707,365 | 12/1972 | Kaufman et al. | 71/123 |
| 3,820,975 | 6/1974 | Poje et al. | 71/88 |
| 3,919,269 | 11/1975 | Jaffe et al. | 260/562 R |
| 3,969,409 | 7/1976 | Miyano et al. | 260/562 R |
| 3,989,737 | 11/1976 | Sawaki et al. | 71/121 |

*Primary Examiner*—Glennon H. Hollrah
*Attorney, Agent, or Firm*—Joel G. Ackerman

[57] ABSTRACT

Compounds having the formula

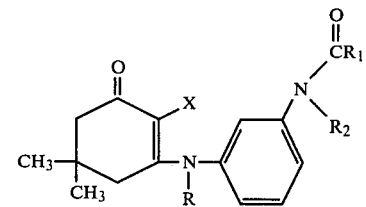

in which X is hydrogen, chloro or bromo; R is hydrogen or lower alkanoyl; $R_1$ is lower alkyl, cyclopropyl or $NR_3R_4$; $R_2$ is hydrogen or lower alkanoyl; and $R_3$ and $R_4$ are independently hydrogen or lower alkyl, are useful as herbicides, primarily for post-emergent application.

15 Claims, No Drawings

NOVEL CYCLOHEXENONE AMINO PHENYL AMIDES AND THEIR USE AS HERBICIDES

DESCRIPTION OF THE INVENTION

This invention relates to novel herbicidal compounds having the formula

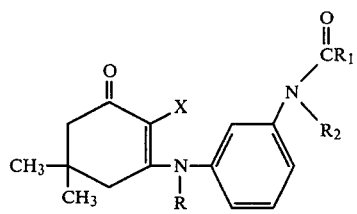

in which X is hydrogen, chloro or bromo; R is hydrogen or lower alkanoyl; $R_1$ is lower alkyl, cyclopropyl or $NR_3R_4$; $R_2$ is hydrogen or lower alkanoyl; and $R_3$ and $R_4$ are independently hydrogen or lower alkyl. $R_3$ and $R_4$ may be the same or different.

By the terms "lower alkyl" and "lower alkanoyl" are meant such groups having from 1 to 4 carbon atoms, including methyl, ethyl and the various propyl and butyl groupings, and acetyl, propionyl, and similar groupings.

The compounds of this group include both amides and ureas, depending on the nature of the $R_1$ constituent of the molecule. If $R_1$ is lower alkyl or cyclopropyl, the compounds are amides. If $R_1$ is a group of the formula $NR_3R_4$, the compounds are ureas. In a preferred embodiment, $R_1$ is lower alkyl, most preferably ethyl.

The compounds of this invention have been found to be active herbicides; that is the compounds have been found to be herbicidally active against various species of weeds. Weeds, in the broadest sense, are plants which grow in locations in which they are not desired. Essentially, as will be seen from the data which follow, these compounds are active as post-emergent herbicides rather than as pre-emergent herbicides. The compounds have been found to affect both broadleaf (dicotyledonous) weeds and grasses (monocotyledons).

This invention also relates to a method for controlling undesirable vegetation comprising applying to such vegetation a herbicidally effective amount of a compound as described herein, and also relates to herbicidal compositions of matter comprising a herbicidally effective amount of a compound as described herein plus an inert diluent or carrier suitable for use with herbicides.

As used herein, the term "herbicide" means a compound which controls or modifies the growth of plants. By the term "herbicidally effective amount" is meant an amount of compound which causes a controlling or modifying effect upon the growth of plants. By the term "plant" is meant germinant seeds, emerging seedlings and established vegetation including roots and aboveground portions. Such modifying and controlling effects include all deviations from natural development.

In general, the compounds of the present invention in which X and R are hydrogen can be prepared by reacting 5,5-dimethyl-1,3-cyclohexanedione with an aminophenyl amide or urea in an aromatic solvent and in the presence of a small amount of acid as a catalyst:

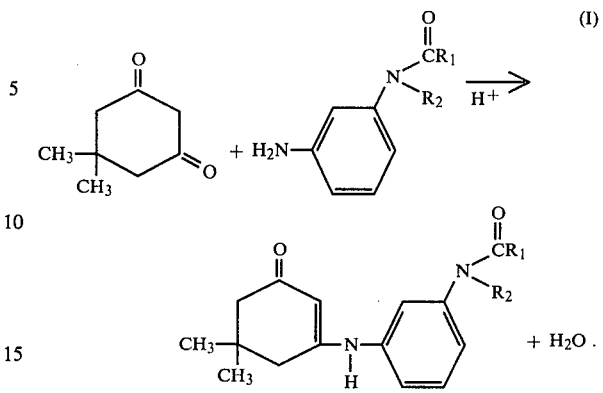

$R_1$ and $R_2$ are as previously defined. The reaction is conducted under reflux, at the boiling point of the solvent, with the water of reaction being continuously removed as an azeotrope with the solvent. The compounds in which X is chloro or bromo can be obtained by chlorination or bromination of the product from the above reaction with an appropriate chlorination or bromination agent in an inert solvent (such as chloroform) under reflux. Compounds in which R is lower alkanoyl are obtained by acylation of either a compound obtained by reaction (I) or of a chlorinated or brominated derivative of such a compound with an acyl chloride under reflux.

The following are examples of the preparation of representative compounds according to the present invention.

EXAMPLE 1

Preparation of N-[3-(3-keto-5,5-dimethylcyclohexenyl)amino] phenyl propionamide (Compound 1 herein):

There were placed in a flask 28 grams (0.2 moles) of 5,5-dimethyl-1,3-cyclohexanedione, 32.8 grams (0.2 mole) of N-(3-aminophenyl) propionamide, 300 milliliters of toluene and 0.5 grams of toluene sulfonic acid monohydrate (as a catalyst). The mixture was heated to reflux, with removal of the toluene-water azeotrope. When the water had been completely removed the flask was cooled and the remaining toluene evaporated under a high vacuum, there was obtained 58 grams of the desired compound, a solid, m.p. 184°–187° C. Structure of the compound was confirmed by infrared, nuclear magnetic resonance and mass spectrometric analyses.

EXAMPLE 2

Preparation of N-[3-(2-bromo-3-keto-5,5-dimethylcyclohexenyl)amino] phenyl propionamide (Compound 8 herein):

In a flask were placed 5 grams of the compound prepared in Example 1, 3.1 grams of N-bromosuccinimide and 40 milliliters of chloroform. The mixture was refluxed for 4 hours, then cooled. 150 milliliters of methylene chloride was added and the mixture washed with two 100-milliliter portions of water. The organic layer was dried and the solvent stripped off to yield 5.3 grams of a yellow sticky solid. Identity of this substance as the desired product was confirmed by nuclear magnetic resonance, infrared and mass spectrometric analyses.

Table I which follows contains a list of representative compounds of the present invention:

TABLE I

[Structure: cyclohexenone with CH₃, CH₃ substituents, X group, and NR-linked phenyl group bearing N(R₁)(C(=O)R₂)... with substituent C(=O)R₁ on nitrogen]

| Compound No. | X | R | R₁ | R₂ | m.p., °C. |
|---|---|---|---|---|---|
| 1 | H | H | $C_2H_5$ | H | 184–187 |
| 2 | H | H | $N(CH_3)_2$ | H | sticky solid |
| 3 | H | H | $NHCH_3$ | H | 198–202 |
| 4 | H | H | —◁ | H | 55–62 |
| 5 | Cl | H | $C_2H_5$ | H | 87–91 |
| 6 | H | $\overset{O}{\underset{}{\overset{\|}{C}}}CC_2H_5$ | $C_2H_5$ | H | 190–193 |
| 7 | H | H | $C_2H_5$ | $\overset{O}{\underset{}{\overset{\|}{C}}}CC_2H_5$ | glass |
| 8 | Br | H | $C_2H_5$ | H | sticky solid |

A. Pre-emergence Herbicide Screening Test:

Using an analytical balance, 20 mg. of the compound to be tested was weighed out on a piece of glassine weighing paper. The paper and compound were placed in a 30-ml. wide-mouth bottle and 3 ml. of acetone containing 1% polyoxyethylene sorbitan monolaurate emulsifying agent was added to dissolve the compound. If the material was not soluble in acetone, another solvent such as water, alcohol or dimethylformamide (DMF) was used instead. When DMF was used, only 0.5 ml. or less was used to dissolve the compound and then another solvent was used to make the volume up to 3 ml. The 3 ml. solution was sprayed uniformly on the soil contained in a small polystyrene flat one day after planting weed seeds in the flat of soil. An atomizer was used to apply the spray using compressed air at a pressure of 5 lb./sq. in. (0.35 kg/cm²). The rate of application was 8 lb./acre (8.96 kg/hectare) and the spray volume was 143 gal./acre (1430 liters/hectare).

On the day preceding treatment, the flat was filled to a depth of 2 inchesd (5.1 cm.) with loamy sand soil. Seeds of seven different weed species were planted in individual rows using one species per row across the width of the flat. The seeds were covered with soil so that they were planted at a depth of 0.5 inch (1.27 cm.). The seeds used were hairy crabgrass (*Digitaria Sanguinalis*), yellow foxtail (*Setaria glauca*), watergrass (*Echinochloa crusgalli*), red oat (*Avena sativa*), redroot pigweed (*Amaranthus retroflexus*), Indian mustard (*Brassica juncea*) and curly dock (*Rumex crispus*). Ample seeds were planted to give about 20 to 50 seedlings per row after emergence depending on the size of the plants.

After treatment, the flats were placed in the greenhouse at a temperature of 70° to 85° F. (21° to 29.5° C.) and watered by sprinkling. Two weeks after treatment the degree of injury or control was determined by comparison with untreated check plants of the same age. The injury from 0 to 100% was recorded for each species as percent control with 0% representing no injury and 100% representing complete kill.

B. Post-Emergence Herbicide Screening Test:

Seeds of six plant species, including hairy crabgrass, watergrass, red oat, mustard, curly dock and pinto beans (*Phaseolus vulgaris*) were planted in polystyrene flats similar to those described above. The flats were placed in the greenhouse at 70° to 85° F. (21° to 29.5° C.) and watered daily with a sprinkler. About 10 to 14 days after planting when the primary leaves of the bean plants were almost fully expanded and the first trifoliate leaves were just starting to form, the plants were sprayed. The spray was prepared by weighing out 20 mg. of the test compound, dissolving it in 5 ml. of acetone containing 1% polyoxyethylene sorbitan monolaurate emulsifying agent and then adding 5 ml. of water. The solution was sprayed on the foliage using an atomizer at an air pressure of 5 lb./sq. in. (0.35 kg/cm²). The spray concentration was 0.1% and the rate was 8 lb./acre, (8.96 kg/hectare). The spray volume was 476 gal./acre (4760 liters/hectare).

TABLE II

| Compound No. | Pre-Emergence Control | Post-Emergence Control |
|---|---|---|
| 1 | 0 | 96 |
| 2 | 0 | 99.5 |
| 3 | 1 | 83 |
| 4 | 0 | 67 |
| 5 | 1 | 33 |
| 6 | 1 | 78 |
| 7 | 0 | 25 |
| 8 | 0 | 57 |

In pre-emergence control, the compounds were essentially inactive with occasional minor activity shown against mustard. Compound 7 did not show a high overall control in the post-emergence test, however, this was due to its selectivity against weeds; it was primarily active against mustard and curly dock and basically inactive against the remaining weeds included in this test.

In practice, a pure compound can be used as a herbicide. However, in general, the compounds are first formulated with one or more inert carriers or diluents suitable for herbicidal use, before being applied.

The compositions or formulations, including a compound as described herein, may take and be used in any one of a number of solid or liquid forms. Examples of solid forms are dusts, granules, tablets, powders and the like. Examples of liquid forms are emulsions, solutions, suspensions, emulsifiable concentrates and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, kieselguhr, clay, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders and pastes are obtained by mixing and grinding an active compound with one or more dispersing agents and/or solid carriers or diluents. Also included are wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes, or higher boiling aromatic hydrocarbons. To obtain suspensions or emulsions in water, wetting agents are also added.

It is possible to use highly concentrated liquid compositions containing up to about 95% by weight of the active compound, or even the 100% active compound alone, when applying the compound in the form of a finely divided liquid by use of various atomizing equipment, for example by airplane crop spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: wettable powders —20 to 90% active compound; oil suspensions, emulsions, solutions and emulsifiable concentrates —5 to 90% active compound; aqueous suspensions —10 to 50% active compound; dusts and powders —1 to 25% active compound; granules and pellets —1 to 20% active compound.

The rate of application of the active compound to a locus to be controlled will depend on the nature of the seeds and plants to be controlled and will vary from about 0.05 to about 50 pounds per acre (about 0.06 to about 56 kg/ha.).

In addition to the active compound and the various agents utilized in preparing compositions and formulations mentioned above, such compositions may also contain one or more other active compounds of the type mentioned herein as well as other active pesticidal agents, such as herbicides, fungicides, insecticides, acaricides, nematocides, bactericides, and plant growth regulators. Such compounds may also contain soil disinfectants or fumigants and may further contain fertilizers, thus making it possible to provide multi-purpose compositions containing one or more of the compounds described herein as well as, optionally, other pesticides and also fertilizers, all intended and formulated for use at the same locus.

Compositions containing one or more of the active compounds described, in a herbicidally effective amount, may be applied to the plant or locus to be controlled in any conventional manner. Thus, powders and various liquid compositions containing the active compound can be applied by the use of powder dusters, boom and hand sprayers and spray dusters, or applied from airplanes as dusts or sprays. When applied in the latter method they may be effective in very low dosages. To modify or control growth of germinating seeds or emerging seedlings liquid compositions may be applied to the soil with conventional methods and may be distributed in the soil to a depth of one-half inch below the soil surface. The compositions need not be admixed with the soil particles but can be applied merely by sprinkling on the surface of the soil.

Compositions including active compounds may also be applied by addition to irrigation waters supplied to the field to be treated. This method of application permits penetration of the compounds into the soil as the water is absorbed therein.

Compositions applied to the surface of the soil can be distributed below the surface of the soil by conventional means such as discing or mixing operations.

What is claimed is:

1. A compound having the formula

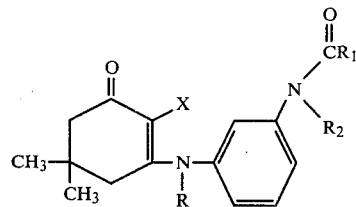

in which X is hydrogen, chloro or bromo; R is hydrogen or lower alkanoyl; $R_1$ is lower alkyl, cyclopropyl or $NR_3R_4$; $R_2$ is hydrogen or lower alkanoyl and $R_3$ and $R_4$ are independently hydrogen or lower alkyl.

2. A compound according to claim 1 in which X, R and $R_2$ are hydrogen and $R_1$ is lower alkyl.

3. A compound according to claim 1 in which X, R and $R_2$ are hydrogen and $R_1$ is $NR_3R_4$.

4. A compound according to claim 1 in which X, R and $R_2$ are each hydrogen and $R_1$ is ethyl.

5. A compound according to claim 1 in which X, R and $R_2$ are each hydrogen and $R_1$ is $N(CH_3)_2$.

6. A compound according to claim 1 in which X, R and $R_2$ are each hydrogen and $R_1$ is $NHCH_1$.

7. A compound according to claim 1 in which X, $R_1$ and $R_2$ are each hydrogen and $R_1$ is cyclopropyl.

8. A compound according to claim 1 in which X is chloro, R and $R_2$ are both hydrogen and $R_1$ is ethyl.

9. A compound according to claim 1 in which X is hydrogen, R is propionyl, $R_1$ is ethyl and $R_2$ is hydrogen.

10. A compound according to claim 1 in which X and R are both hydrogen, $R_1$ is ethyl and $R_2$ is propionyl.

11. A compound according to claim 1 in which X is bromo, R and $R_2$ are hydrogen, and $R_1$ is ethyl.

12. A method of controlling undesirable vegetation comprising applying to the vegetation a herbicidally effective amount of a compound having the formula

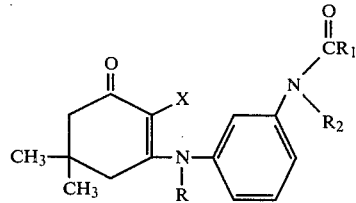

in which X is hydrogen, chloro or bromo; R is hydrogen or lower alkanoyl; $R_1$ is lower alkyl, cyclopropyl or $NR_3R_4$; $R_2$ is hydrogen or lower alkanoyl and $R_3$ and $R_4$ are independently hydrogen or lower alkyl.

13. A method according to claim 12 in which X, R and $R_2$ are each hydrogen and $R_1$ is lower alkyl.

14. A method according to claim 12 in which X, R and $R_2$ are each hydrogen and $R_1$ is $NR_3R_4$.

15. A herbicidal composition of matter comprising:

(a) a herbicidally effective amount of a compound having the formula in which X is hydrogen, chloro or bromo; R is hydrogen or lower alkanoyl; $R_1$ is lower alkyl, cyclopropyl or $NR_3R_4$, $R_2$ is hydrogen or lower alkanoyl and $R_3$ and $R_4$ are independently hydrogen or lower alkyl; and (b) a herbicidally suitable inert carrier or diluent.

* * * * *

UNITED STATES PATENT AND TRADEMARK OFFICE
CERTIFICATE OF CORRECTION

PATENT NO. : 4,265,658
DATED : May 5, 1981
INVENTOR(S) : Raymond A. Felix

It is certified that error appears in the above-identified patent and that said Letters Patent are hereby corrected as shown below:

Column 3, line 47, please change ---inchesd--- to read ---inches---.

Column 6, Claim 6, please change ---$R_1$ is $NHCH_1$--- to read ---$R_1$ is $NHCH_3$.

Signed and Sealed this

Thirteenth Day of October 1981

[SEAL]

Attest:

GERALD J. MOSSINGHOFF

Attesting Officer

Commissioner of Patents and Trademarks